United States Patent
Mullen et al.

(10) Patent No.: US 12,121,328 B2
(45) Date of Patent: Oct. 22, 2024

(54) CREDIT, SECURITY, DEBIT CARDS AND THE LIKE WITH BUTTONS

(75) Inventors: Jeffrey David Mullen, Pittsburgh, PA (US); Will Reutzel, Pittsburgh, PA (US)

(73) Assignee: Dynamics Inc., Pittsburgh, PA (US)

( * ) Notice: Subject to any disclaimer, the term of this patent is extended or adjusted under 35 U.S.C. 154(b) by 0 days.

(21) Appl. No.: 12/339,092

(22) Filed: Dec. 19, 2008

(65) Prior Publication Data

US 2009/0160617 A1    Jun. 25, 2009

Related U.S. Application Data

(60) Provisional application No. 61/120,813, filed on Dec. 8, 2008, provisional application No. 61/119,366, filed
(Continued)

(51) Int. Cl.
*G06K 19/07* (2006.01)
*A61B 5/02* (2006.01)
(Continued)

(52) U.S. Cl.
CPC ............ *A61B 5/02042* (2013.01); *A61B 5/02* (2013.01); *G06F 3/0488* (2013.01); *G06K 7/0004* (2013.01); *G06K 7/084* (2013.01); *G06K 7/087* (2013.01); *G06K 7/10297* (2013.01); *G06K 19/06187* (2013.01); *G06K 19/06206* (2013.01); *G06K 19/07* (2013.01);
(Continued)

(58) Field of Classification Search
CPC ...... G07F 7/005; G07F 7/0833; G07F 7/1008; G06Q 20/409; G06F 9/54

USPC ......................................... 340/5.85; 235/449
See application file for complete search history.

(56) References Cited

U.S. PATENT DOCUMENTS 4,353,064 A    10/1982   Stamm
4,394,654 A    7/1983    Hofmann-Cerfontaine
(Continued)

FOREIGN PATENT DOCUMENTS

EP    0203683    12/1986
GB    2420098    5/2006
(Continued)

OTHER PUBLICATIONS

U.S. Appl. No. 60/594,300, Poidomani et al.
(Continued)

*Primary Examiner* — Vernal U Brown
(74) *Attorney, Agent, or Firm* — Morris Law Group; Robert W. Morris (57) ABSTRACT

A card is provided, such as a credit card or security card, that may transmit information to a magnetic stripe reader via a magnetic emulator. The emulator may transmit the information in order to reduce the amount of circuitry needed to emulate a particular block of information. Additionally, for example, one or more buttons may be included on the card. Buttons may be includes, for example, to provide a control interface to navigate through various options of the card. Additionally, coding schemes may be selected via buttons. Furthermore, a card may be locked until a private number is entered into a card or a number may only be generated (e.g., displayed and/or emulated) once a particular private number is entered into a card.

17 Claims, 9 Drawing Sheets

Related U.S. Application Data on Dec. 2, 2008, provisional application No. 61/117,186, filed on Nov. 23, 2008, provisional application No. 61/112,766, filed on Nov. 9, 2008, provisional application No. 61/097,401, filed on Sep. 16, 2008, provisional application No. 61/090,423, filed on Aug. 20, 2008, provisional application No. 61/086,239, filed on Aug. 5, 2008, provisional application No. 61/081,003, filed on Jul. 15, 2008, provisional application No. 61/027,807, filed on Feb. 11, 2008, provisional application No. 61/026,846, filed on Feb. 7, 2008, provisional application No. 61/016,491, filed on Dec. 24, 2007.

(51) Int. Cl.

| | |
|---|---|
| G06F 3/0488 | (2022.01) |
| G06K 7/00 | (2006.01) |
| G06K 7/08 | (2006.01) |
| G06K 7/10 | (2006.01) |
| G06K 19/06 | (2006.01) |
| G06K 19/073 | (2006.01) |
| G06K 19/077 | (2006.01) |
| G06K 19/08 | (2006.01) |
| G06Q 20/18 | (2012.01) |
| G06Q 20/20 | (2012.01) |
| G06Q 20/34 | (2012.01) |
| G06Q 20/38 | (2012.01) |
| G06Q 20/40 | (2012.01) |
| G06Q 30/0207 | (2023.01) |
| G06Q 30/0241 | (2023.01) |
| G06Q 30/0601 | (2023.01) |
| G06T 7/62 | (2017.01) |
| G06V 10/24 | (2022.01) |
| G06V 10/25 | (2022.01) |
| G07F 7/08 | (2006.01) |
| G07F 7/10 | (2006.01) |

(52) U.S. Cl.
CPC ..... *G06K 19/0702* (2013.01); *G06K 19/0704* (2013.01); *G06K 19/0723* (2013.01); *G06K 19/0725* (2013.01); *G06K 19/07345* (2013.01); *G06K 19/07703* (2013.01); *G06K 19/07705* (2013.01); *G06K 19/07707* (2013.01); *G06K 19/07709* (2013.01); *G06K 19/07749* (2013.01); *G06K 19/0775* (2013.01); *G06K 19/07766* (2013.01); *G06K 19/07769* (2013.01); *G06K 19/07773* (2013.01); *G06K 19/083* (2013.01); *G06Q 20/18* (2013.01); *G06Q 20/20* (2013.01); *G06Q 20/34* (2013.01); *G06Q 20/341* (2013.01); *G06Q 20/3415* (2013.01); *G06Q 20/352* (2013.01); *G06Q 20/385* (2013.01); *G06Q 20/401* (2013.01); *G06Q 30/0222* (2013.01); *G06Q 30/0241* (2013.01); *G06Q 30/0277* (2013.01); *G06Q 30/0641* (2013.01); *G06T 7/62* (2017.01); *G06V 10/24* (2022.01); *G06V 10/25* (2022.01); *G07F 7/0806* (2013.01); *G07F 7/1008* (2013.01); *G06T 2207/10024* (2013.01); *G06T 2207/30004* (2013.01); *G06V 2201/03* (2022.01)

(56) References Cited

U.S. PATENT DOCUMENTS

| | | |
|---|---|---|
| 4,614,861 A | 9/1986 | Pavlov et al. |
| 4,667,087 A | 5/1987 | Francini et al. |
| 4,697,072 A | 9/1987 | Kawana |
| 4,701,601 A | 10/1987 | Francini et al. |
| 4,720,860 A | 1/1988 | Weiss |
| 4,766,293 A | 8/1988 | Boston |
| 4,786,791 A | 11/1988 | Hodama |
| 4,791,283 A | 12/1988 | Burkhardt |
| 4,797,542 A | 1/1989 | Hara |
| 4,868,376 A | 9/1989 | Lessin et al. |
| 4,902,146 A | 2/1990 | Ishikawa |
| 5,038,251 A | 8/1991 | Sugiyama et al. |
| 5,072,103 A | 12/1991 | Nara |
| 5,168,520 A | 12/1992 | Weiss |
| 5,237,614 A | 8/1993 | Weiss |
| 5,254,843 A | 10/1993 | Hynes et al. |
| 5,276,311 A | 1/1994 | Hennige |
| 5,347,580 A | 9/1994 | Molva et al. |
| 5,361,062 A | 11/1994 | Weiss et al. |
| 5,362,952 A * | 11/1994 | Nair et al. ..................... 235/449 |
| 5,412,199 A | 5/1995 | Finkelstein et al. |
| 5,434,398 A | 7/1995 | Goldberg |
| 5,434,405 A | 7/1995 | Finkelstein et al. |
| 5,477,038 A | 12/1995 | Levine et al. |
| 5,478,994 A | 12/1995 | Rahman |
| 5,479,512 A | 12/1995 | Weiss |
| 5,484,997 A | 1/1996 | Haynes |
| 5,485,519 A | 1/1996 | Weiss |
| 5,585,787 A | 12/1996 | Wallerstein |
| 5,590,038 A | 12/1996 | Pitroda |
| 5,591,949 A | 1/1997 | Bernstein |
| 5,608,203 A | 3/1997 | Finkelstein et al. |
| 5,623,552 A | 4/1997 | Lane |
| 5,657,388 A | 8/1997 | Weiss |
| 5,748,737 A | 5/1998 | Daggar |
| 5,834,747 A | 11/1998 | Cooper |
| 5,834,756 A | 11/1998 | Gutman et al. |
| 5,856,661 A | 1/1999 | Finkelstein et al. |
| 5,864,623 A | 1/1999 | Messina et al. |
| 5,907,142 A | 5/1999 | Kelsey |
| 5,913,203 A | 6/1999 | Wong et al. |
| 5,937,394 A | 8/1999 | Wong et al. |
| 5,955,021 A | 9/1999 | Tiffany, III |
| 5,955,961 A | 9/1999 | Wallerstein |
| 5,956,699 A | 9/1999 | Wong et al. |
| 6,012,636 A | 1/2000 | Smith |
| 6,019,284 A * | 2/2000 | Freeman et al. ............ 235/380 |
| 6,025,054 A | 2/2000 | Tiffany, III |
| 6,045,043 A | 4/2000 | Bashan et al. |
| 6,070,794 A | 6/2000 | Niwata et al. |
| 6,076,163 A | 6/2000 | Hoffstein et al. |
| 6,079,621 A * | 6/2000 | Vardanyan ........... G06K 19/073 235/487 |
| 6,085,320 A | 7/2000 | Kaliski |
| 6,095,416 A | 8/2000 | Grant et al. |
| 6,129,277 A | 10/2000 | Grant et al. |
| 6,130,621 A | 10/2000 | Weiss |
| 6,145,079 A | 11/2000 | Mitty et al. |
| 6,157,920 A | 12/2000 | Jakobsson et al. |
| 6,161,181 A | 12/2000 | Haynes, III et al. |
| 6,176,430 B1 | 1/2001 | Finkelstein et al. |
| 6,182,894 B1 | 2/2001 | Hackett et al. |
| 6,189,098 B1 | 2/2001 | Kaliski |
| 6,199,052 B1 | 3/2001 | Mitty et al. |
| 6,206,293 B1 | 3/2001 | Gutman et al. |
| 6,240,184 B1 | 5/2001 | Huynh et al. |
| 6,241,153 B1 | 6/2001 | Tiffany, III |
| 6,256,873 B1 | 7/2001 | Tiffany, III |
| 6,269,163 B1 | 7/2001 | Rivest et al. |
| 6,286,022 B1 | 9/2001 | Kaliski et al. |
| 6,308,890 B1 | 10/2001 | Cooper |
| 6,313,724 B1 | 11/2001 | Osterweil |
| 6,353,811 B1 | 3/2002 | Weissman |
| 6,389,442 B1 | 5/2002 | Yin et al. |
| 6,393,447 B1 | 5/2002 | Jakobsson et al. |
| 6,402,029 B1 | 6/2002 | Gangi |
| 6,411,715 B1 | 6/2002 | Liskov et al. |
| 6,446,052 B1 | 9/2002 | Juels |
| 6,460,141 B1 | 10/2002 | Olden |
| 6,592,044 B1 | 7/2003 | Wong et al. |
| 6,607,127 B2 | 8/2003 | Wong |

(56) References Cited

U.S. PATENT DOCUMENTS

| | | |
|---|---|---|
| 6,609,654 B1 | 8/2003 | Anderson et al. |
| 6,631,849 B2 | 10/2003 | Blossom |
| 6,654,797 B1 | 11/2003 | Kamper |
| 6,655,585 B2 | 12/2003 | Shinn |
| 6,681,988 B2 | 1/2004 | Stack et al. |
| 6,705,520 B1 | 3/2004 | Pitroda et al. |
| 6,755,341 B1 | 6/2004 | Wong et al. |
| 6,764,005 B2 | 7/2004 | Cooper |
| 6,769,618 B1 | 8/2004 | Finkelstein |
| 6,805,288 B2 | 10/2004 | Routhenstein et al. |
| 6,811,082 B2 | 11/2004 | Wong |
| 6,813,354 B1 | 11/2004 | Jakobsson et al. |
| 6,817,532 B2 | 11/2004 | Finkelstein |
| 6,873,974 B1 | 3/2005 | Schutzer |
| 6,902,116 B2 | 6/2005 | Finkelstein |
| 6,970,070 B2 | 11/2005 | Juels et al. |
| 6,975,202 B1 | 12/2005 | Rodriguez et al. |
| 6,980,969 B1 | 12/2005 | Tuchler et al. |
| 6,985,583 B1 | 1/2006 | Brainard et al. |
| 6,991,155 B2 | 1/2006 | Burchette, Jr. |
| 7,013,030 B2 | 3/2006 | Wong et al. |
| 7,035,443 B2 | 4/2006 | Wong |
| 7,039,221 B1 | 5/2006 | Tumey et al. |
| 7,039,223 B2 | 5/2006 | Wong |
| 7,044,394 B2 | 5/2006 | Brown |
| 7,051,929 B2 * | 5/2006 | Li ................................. 235/380 |
| 7,083,094 B2 | 8/2006 | Cooper |
| 7,100,049 B2 | 8/2006 | Gasparini et al. |
| 7,100,821 B2 | 9/2006 | Rasti |
| 7,111,172 B1 | 9/2006 | Duane et al. |
| 7,114,652 B2 | 10/2006 | Moullette et al. |
| 7,136,514 B1 | 11/2006 | Wong |
| 7,140,550 B2 | 11/2006 | Ramachandran |
| 7,163,153 B2 | 1/2007 | Blossom |
| 7,195,154 B2 | 3/2007 | Juels et al. |
| 7,197,639 B1 | 3/2007 | Juels et al. |
| 7,219,368 B2 | 5/2007 | Juels et al. |
| 7,225,537 B2 | 6/2007 | Reed |
| 7,225,994 B2 | 6/2007 | Finkelstein |
| 7,246,752 B2 | 7/2007 | Brown |
| 7,298,243 B2 | 11/2007 | Juels et al. |
| 7,334,732 B2 | 2/2008 | Cooper |
| 7,337,326 B2 | 2/2008 | Palmer et al. |
| 7,346,775 B2 | 3/2008 | Gasparinl et al. |
| 7,347,382 B2 | 3/2008 | Ferber et al. |
| 7,356,696 B1 | 4/2008 | Jakobsson et al. |
| 7,357,319 B1 | 4/2008 | Liu et al. |
| 7,359,507 B2 | 4/2008 | Kaliski |
| 7,360,688 B1 | 4/2008 | Harris |
| 7,363,494 B2 | 4/2008 | Brainard et al. |
| 7,364,092 B2 | 4/2008 | Narendra et al. |
| 7,380,710 B2 | 6/2008 | Brown |
| 7,398,253 B1 | 7/2008 | Pinnell |
| 7,404,087 B2 | 7/2008 | Teunen |
| 7,424,570 B2 | 9/2008 | D'Albore et al. |
| 7,427,033 B1 | 9/2008 | Roskind |
| 7,454,349 B2 | 11/2008 | Teunen et al. |
| 7,461,250 B1 | 12/2008 | Duane et al. |
| 7,461,399 B2 | 12/2008 | Juels et al. |
| 7,472,093 B2 | 12/2008 | Juels |
| 7,472,829 B2 | 1/2009 | Brown |
| 7,494,055 B2 | 2/2009 | Fernandes et al. |
| 7,502,467 B2 | 3/2009 | Brainard et al. |
| 7,502,933 B2 | 3/2009 | Jakobsson et al. |
| 7,503,485 B1 | 3/2009 | Routhenstein |
| 7,516,492 B1 | 4/2009 | Nisbet et al. |
| 7,523,301 B2 | 4/2009 | Nisbet et al. |
| 7,530,495 B2 | 5/2009 | Cooper |
| 7,532,104 B2 | 5/2009 | Juels |
| 7,543,739 B2 | 6/2009 | Brown et al. |
| 7,559,464 B2 | 7/2009 | Routhenstein |
| 7,562,221 B2 | 7/2009 | Nystrom et al. |
| 7,562,222 B2 | 7/2009 | Gasparini et al. |
| 7,580,898 B2 | 8/2009 | Brown et al. |
| 7,584,153 B2 | 9/2009 | Brown et al. |
| 7,591,416 B2 | 9/2009 | Blossom |
| 7,591,426 B2 | 9/2009 | Osterweil et al. |
| 7,591,427 B2 | 9/2009 | Osterweil |
| 7,602,904 B2 | 10/2009 | Juels et al. |
| 7,631,804 B2 | 12/2009 | Brown |
| 7,639,537 B2 | 12/2009 | Sepe et al. |
| 7,641,124 B2 | 1/2010 | Brown et al. |
| 7,660,902 B2 | 2/2010 | Graham et al. |
| 7,681,232 B2 | 3/2010 | Nordentoft et al. |
| 7,784,687 B2 | 8/2010 | Mullen et al. |
| 7,828,207 B2 | 11/2010 | Cooper |
| 7,913,919 B2 | 3/2011 | Carmichael et al. |
| 7,954,724 B2 | 6/2011 | Poidomani et al. |
| 8,494,959 B2 | 7/2013 | Hathaway et al. |
| 2001/0034702 A1 | 10/2001 | Mockett et al. |
| 2001/0047335 A1 | 11/2001 | Arndt et al. |
| 2002/0003169 A1 | 1/2002 | Cooper |
| 2002/0032657 A1 | 3/2002 | Singh |
| 2002/0043566 A1 | 4/2002 | Goodman et al. |
| 2002/0059114 A1 | 5/2002 | Cockrill et al. |
| 2002/0082989 A1 | 6/2002 | Fife et al. |
| 2002/0095580 A1 | 7/2002 | Candelore |
| 2002/0096570 A1 | 7/2002 | Wong et al. |
| 2002/0120583 A1 | 8/2002 | Keresman, III et al. |
| 2002/0139844 A1 | 10/2002 | Rochman et al. |
| 2002/0153424 A1 | 10/2002 | Chuan |
| 2002/0180584 A1 | 12/2002 | McGregor et al. |
| 2002/0195493 A1 | 12/2002 | Dell |
| 2003/0004827 A1 * | 1/2003 | Wang ............................... 705/26 |
| 2003/0034388 A1 | 2/2003 | Routhenstein et al. |
| 2003/0052168 A1 | 3/2003 | Wong |
| 2003/0057278 A1 | 3/2003 | Wong |
| 2003/0085286 A1 | 5/2003 | Kelley et al. |
| 2003/0116635 A1 | 6/2003 | Taban |
| 2003/0132301 A1 | 7/2003 | Selker |
| 2003/0136503 A1 | 7/2003 | Green et al. |
| 2003/0152253 A1 | 8/2003 | Wong |
| 2003/0163287 A1 | 8/2003 | Vock et al. |
| 2003/0173409 A1 | 9/2003 | Vogt et al. |
| 2003/0179909 A1 | 9/2003 | Wong et al. |
| 2003/0179910 A1 | 9/2003 | Wong |
| 2003/0209608 A1 | 11/2003 | Blossom |
| 2003/0218066 A1 | 11/2003 | Fernandes et al. |
| 2003/0226899 A1 | 12/2003 | Finkelstein |
| 2004/0011877 A1 | 1/2004 | Reppermund |
| 2004/0035942 A1 | 2/2004 | Silverman |
| 2004/0124250 A1 | 7/2004 | Kojima et al. |
| 2004/0133787 A1 | 7/2004 | Doughty |
| 2004/0159700 A1 | 8/2004 | Khan et al. |
| 2004/0162732 A1 | 8/2004 | Rahim et al. |
| 2004/0172535 A1 | 9/2004 | Jakobsson |
| 2004/0177045 A1 | 9/2004 | Brown |
| 2005/0001711 A1 | 1/2005 | Doughty et al. |
| 2005/0015612 A1 | 1/2005 | You |
| 2005/0043997 A1 | 2/2005 | Sohata et al. |
| 2005/0080747 A1 | 4/2005 | Anderson et al. |
| 2005/0086160 A1 | 4/2005 | Wong et al. |
| 2005/0086177 A1 | 4/2005 | Anderson et al. |
| 2005/0092830 A1 | 5/2005 | Blossom |
| 2005/0116026 A1 | 6/2005 | Burger et al. |
| 2005/0119940 A1 | 6/2005 | Concilio et al. |
| 2005/0133590 A1 | 6/2005 | Rettenmyer et al. |
| 2005/0133606 A1 | 6/2005 | Brown |
| 2005/0154643 A1 | 7/2005 | Doan et al. |
| 2005/0194452 A1 | 9/2005 | Nordentoft et al. |
| 2005/0211785 A1 * | 9/2005 | Ferber et al. ................. 235/492 |
| 2005/0219728 A1 | 10/2005 | Durbin et al. |
| 2005/0228959 A1 | 10/2005 | D'Albore et al. |
| 2005/0234769 A1 * | 10/2005 | Jain et al. ....................... 705/14 |
| 2005/0240527 A1 | 10/2005 | Goldman |
| 2006/0000900 A1 | 1/2006 | Fernandes et al. |
| 2006/0037073 A1 | 2/2006 | Juels et al. |
| 2006/0041759 A1 | 2/2006 | Kaliski et al. |
| 2006/0081700 A1 | 4/2006 | Li |
| 2006/0085328 A1 | 4/2006 | Cohen et al. |
| 2006/0091223 A1 | 5/2006 | Zellner |
| 2006/0131393 A1 | 6/2006 | Cok et al. |
| 2006/0161435 A1 | 7/2006 | Atef et al. |

(56) References Cited

U.S. PATENT DOCUMENTS

| | | | |
|---|---|---|---|
| 2006/0161789 A1* | 7/2006 | Doughty | G06Q 20/341 713/186 |
| 2006/0163353 A1 | 7/2006 | Moulette et al. | |
| 2006/0174104 A1 | 8/2006 | Crichton et al. | |
| 2006/0186209 A1 | 8/2006 | Narendra et al. | |
| 2006/0192006 A1 | 8/2006 | Brown | |
| 2006/0196931 A1 | 9/2006 | Holtmanns et al. | |
| 2006/0226217 A1 | 10/2006 | Narendra et al. | |
| 2006/0227523 A1 | 10/2006 | Pennaz et al. | |
| 2006/0249574 A1 | 11/2006 | Brown et al. | |
| 2006/0256961 A1 | 11/2006 | Brainard et al. | |
| 2006/0269061 A1 | 11/2006 | Balasubramanian et al. | |
| 2006/0278698 A1 | 12/2006 | Lovett | |
| 2006/0283958 A1 | 12/2006 | Osterweil | |
| 2007/0023532 A1 | 2/2007 | Narendra et al. | |
| 2007/0034700 A1 | 2/2007 | Poidomani et al. | |
| 2007/0052613 A1 | 3/2007 | Gallschuetz et al. | |
| 2007/0073619 A1 | 3/2007 | Smith | |
| 2007/0095892 A1* | 5/2007 | Lyons | G06Q 20/16 455/414.1 |
| 2007/0114274 A1 | 5/2007 | Gibbs et al. | |
| 2007/0124321 A1 | 5/2007 | Szydlo | |
| 2007/0131759 A1 | 6/2007 | Cox et al. | |
| 2007/0136211 A1 | 6/2007 | Brown et al. | |
| 2007/0152070 A1 | 7/2007 | D'Albore | |
| 2007/0152072 A1 | 7/2007 | Frallicciardi et al. | |
| 2007/0153487 A1 | 7/2007 | Frallicciardi et al. | |
| 2007/0174614 A1 | 7/2007 | Duane et al. | |
| 2007/0189581 A1 | 8/2007 | Nordentoft et al. | |
| 2007/0200839 A1 | 8/2007 | Sampsell | |
| 2007/0203850 A1 | 8/2007 | Singh et al. | |
| 2007/0241183 A1 | 10/2007 | Brown et al. | |
| 2007/0241201 A1 | 10/2007 | Brown et al. | |
| 2007/0256123 A1 | 11/2007 | Duane et al. | |
| 2007/0262138 A1 | 11/2007 | Somers et al. | |
| 2007/0262139 A1 | 11/2007 | Fiebiger et al. | |
| 2007/0192249 A1 | 12/2007 | Biffle et al. | |
| 2007/0291753 A1 | 12/2007 | Romano | |
| 2008/0005510 A1 | 1/2008 | Sepe et al. | |
| 2008/0008315 A1 | 1/2008 | Fontana et al. | |
| 2008/0008322 A1 | 1/2008 | Fontana et al. | |
| 2008/0010675 A1 | 1/2008 | Massascusa et al. | |
| 2008/0016351 A1 | 1/2008 | Fontana et al. | |
| 2008/0019507 A1 | 1/2008 | Fontana et al. | |
| 2008/0028447 A1 | 1/2008 | O'Malley et al. | |
| 2008/0029598 A1 | 2/2008 | Fernandes et al. | |
| 2008/0040271 A1 | 2/2008 | Hammad et al. | |
| 2008/0040276 A1 | 2/2008 | Hammad et al. | |
| 2008/0058016 A1 | 3/2008 | Di Maggio et al. | |
| 2008/0059379 A1 | 3/2008 | Ramaci et al. | |
| 2008/0093467 A1 | 4/2008 | Narendra et al. | |
| 2008/0096326 A1 | 4/2008 | Reed | |
| 2008/0099556 A1 | 5/2008 | Park | |
| 2008/0121726 A1 | 5/2008 | Brady et al. | |
| 2008/0126260 A1 | 5/2008 | Cox et al. | |
| 2008/0126398 A1 | 5/2008 | Cimino | |
| 2008/0128515 A1 | 6/2008 | Di Iorio | |
| 2008/0148394 A1 | 6/2008 | Poidomani et al. | |
| 2008/0201264 A1 | 8/2008 | Brown et al. | |
| 2008/0209550 A1 | 8/2008 | Di Iorio | |
| 2008/0210754 A1 | 9/2008 | Lovett | |
| 2008/0223937 A1 | 9/2008 | Preta et al. | |
| 2008/0288699 A1 | 11/2008 | Chichierchia | |
| 2008/0290166 A1 | 11/2008 | von Mueller | |
| 2008/0294930 A1 | 11/2008 | Varone et al. | |
| 2008/0302877 A1 | 12/2008 | Musella et al. | |
| 2008/0314976 A1 | 12/2008 | Capurso et al. | |
| 2009/0006262 A1 | 1/2009 | Brown et al. | |
| 2009/0013122 A1 | 1/2009 | Sepe et al. | |
| 2009/0036147 A1 | 2/2009 | Romano | |
| 2009/0046522 A1 | 2/2009 | Sepe et al. | |
| 2009/0048971 A1 | 2/2009 | Hathaway et al. | |
| 2009/0055893 A1 | 2/2009 | Manessis et al. | |
| 2009/0078761 A1 | 3/2009 | Sines | |
| 2009/0078777 A1 | 3/2009 | Granucci et al. | |
| 2009/0108064 A1 | 4/2009 | Fernandes et al. | |
| 2009/0150295 A1 | 6/2009 | Hatch et al. | |
| 2009/0152365 A1 | 6/2009 | Li et al. | |
| 2009/0159667 A1 | 6/2009 | Mullen et al. | |
| 2009/0159669 A1 | 6/2009 | Mullen | |
| 2009/0159678 A1 | 6/2009 | Day et al. | |
| 2009/0164380 A1 | 6/2009 | Brown | |
| 2009/0187507 A1 | 7/2009 | Brown | |
| 2009/0248581 A1 | 10/2009 | Brown | |
| 2009/0255996 A1 | 10/2009 | Brown et al. | |
| 2009/0294524 A1 | 12/2009 | Rice et al. | |
| 2009/0298540 A1 | 12/2009 | Narendra et al. | |
| 2009/0314840 A1 | 12/2009 | Granucci et al. | |
| 2010/0065628 A1 | 3/2010 | Carmichael et al. | |
| 2010/0127083 A1 | 5/2010 | Brown et al. | |
| 2010/0230487 A1 | 9/2010 | Johnson et al. | |
| 2010/0270303 A1 | 10/2010 | Poidomani et al. | |
| 2011/0028184 A1 | 2/2011 | Cooper | |
| 2011/0047036 A1* | 2/2011 | Foran-Owens | G06Q 20/18 705/17 |
| 2011/0053644 A1 | 3/2011 | Narendra et al. | |
| 2011/0066512 A1 | 3/2011 | Kanngard | |
| 2011/0073663 A1 | 3/2011 | Narendra et al. | |
| 2011/0073665 A1 | 3/2011 | Narendra et al. | |
| 2011/0108626 A1 | 5/2011 | Hepner et al. | |
| 2011/0140841 A1 | 6/2011 | Bona et al. | |
| 2011/0220726 A1 | 9/2011 | Narendra et al. | |
| 2011/0266354 A1 | 11/2011 | Poidomani et al. | |
| 2012/0037709 A1 | 2/2012 | Cloutier et al. | |
| 2012/0234927 A1 | 9/2012 | Poidomani et al. | |
| 2012/0235794 A1 | 9/2012 | Poidomani et al. | |
| 2012/0241519 A1 | 9/2012 | Lawson et al. | |
| 2012/0241523 A1 | 9/2012 | Poidomani et al. | |

FOREIGN PATENT DOCUMENTS

| | | |
|---|---|---|
| JP | 05210770 A | 8/1993 |
| WO | WO9852735 | 11/1998 |
| WO | WO0247019 | 6/2002 |
| WO | WO06066322 | 6/2006 |
| WO | WO06080929 | 8/2006 |
| WO | WO06105092 | 10/2006 |
| WO | WO06116772 | 11/2006 |
| WO | WO07141779 | 12/2007 |

OTHER PUBLICATIONS

U.S. Appl. No. 60/675,388, Poidomani et al.
English translation of JP 05210770 A.
The Bank Credit Card Business. Second Edition, American Bankers Association, Washington, D.C., 1996.
A Day in the Life of a Flux Reversal. http://www.phrack.org/issues.html?issue=37&id=6#article. As viewed on Apr. 12, 2010.
Dynamic Virtual Credit Card Numbers. http://homes.cerias.purdue.edu/~jtli/paper/fc07.pdf. As viewed on Apr. 12, 2010.
USPTO, International Search Report, Apr. 28, 2009.
Extended European Search Report for European Patent Application No. 08865573.3, Jan. 26, 2012.
EPO, Article 94(3) Communication, Feb. 5, 2013.
EPO, Rule 115(1) Summons to Oral Proceedings, Sep. 18, 2013.
Magnetic Stripe Card. http://en.wikipedia.org/w/index.php?title=Magnetic_stripe_card&oldid= 174608901. Dated Nov. 29, 2007.
See EPO, Article 94(3) Communication, Feb. 5, 2013.
Au, Patent Examination Report No. 1, Oct. 11, 2012.

* cited by examiner

CREDIT, SECURITY, DEBIT CARDS AND THE LIKE WITH BUTTONS

CROSS-REFERENCE TO RELATED APPLICATIONS

This application claims the benefit of U.S. Provisional Patent Application Nos. 61/016,491 filed on Dec. 24, 2007, 61/026,846 filed on Feb. 7, 2008, 61/027,807 filed on Feb. 11, 2008, 61/081,003 filed on Jul. 15, 2008, 61/086,239 filed on Aug. 5, 2008, 61/090,423 filed on Aug. 20, 2008, 61/097,401 filed Sep. 16, 2008, 61/112,766 filed on Nov. 9, 2008, 61/117,186 filed on Nov. 23, 2008, 61/119,366 filed on Dec. 2, 2008, and 61/120,813 filed on Dec. 8, 2008, all of which are hereby incorporated by reference herein in their entirety.

BACKGROUND OF THE INVENTION

This invention relates to cards such as payment and security cards.

SUMMARY OF THE INVENTION

A card is provided, such as a credit card or security card, that may transmit information to a magnetic stripe reader via a dynamic magnetic communications device such as a magnetic emulator or a magnetic encoder. The emulator may transmit the information serially, for example, in order to reduce the amount of circuitry needed to emulate a particular block of information (e.g., payment information).

One or more buttons may be included on the card. Buttons may be included, for example, to provide a control interface to navigate through various options of the card. Additionally, coding schemes may be selected via buttons. Furthermore, a card may be locked until a private number is entered into a card or a number may only be generated (e.g., displayed and/or emulated) once a particular private number is entered into a card. Such a number may be, for example, a dynamic credit card, security card, and/or debit card number or other number (e.g., security code).

A card, or other device, having a magnetic emulator may take the form of, for example, a credit card, debit card, and/or security card. Accordingly, the dynamic information may be a dynamic credit card number, a dynamic debit card number, and/or a dynamic security number. A display may be provided to display the data, or a portion of the data, communicated through an emulator. In this manner, a credit card may be provided that includes a display. All, or a portion of, a credit card number may, for example, be changed periodically and displayed on the display. Similarly, this changed information may be emulated via a parallel or serial emulator or other dynamic magnetic communications device (e.g., a magnetic encoder).

A dynamic magnetic communications device (e.g., magnetic emulators and/or encoders) may be located next to one or more magnetic stripe segments (e.g., sandwiched between two magnetic stripe segments from a birds-eye perspective of a card). A magnetic stripe may be utilized to transmit static information such that power is conserved. For example, if the beginning bits of a data block must take a particular form (e.g., start bits followed by user identification information) then this information may be embodied as a magnetic stripe. A serial or parallel emulator or encoder may then be provided to communicate the remaining information of the block (e.g., dynamic credit card number).

Numerous types of structures may be utilized to determine when a read-head of a magnetic stripe reader is reading, or is about to read, a magnetic stripe or dynamic magnetic communications device. Such structures may be utilized to turn a magnetic emulator, ON and OFF. By only turning an emulator ON when the emulator is in the proximity of a magnetic stripe reader, power may be conserved. For example, a button may be provided on a card, or other device, such that a user may provide manual input to instruct the card, or other device, to turn an emulator ON.

BRIEF DESCRIPTION OF THE DRAWINGS

The principles and advantages of the present invention can be more clearly understood from the following detailed description considered in conjunction with the following drawings, in which the same reference numerals denote the same structural elements throughout, and in which.

DETAILED DESCRIPTION OF THE INVENTION

Figure 1:
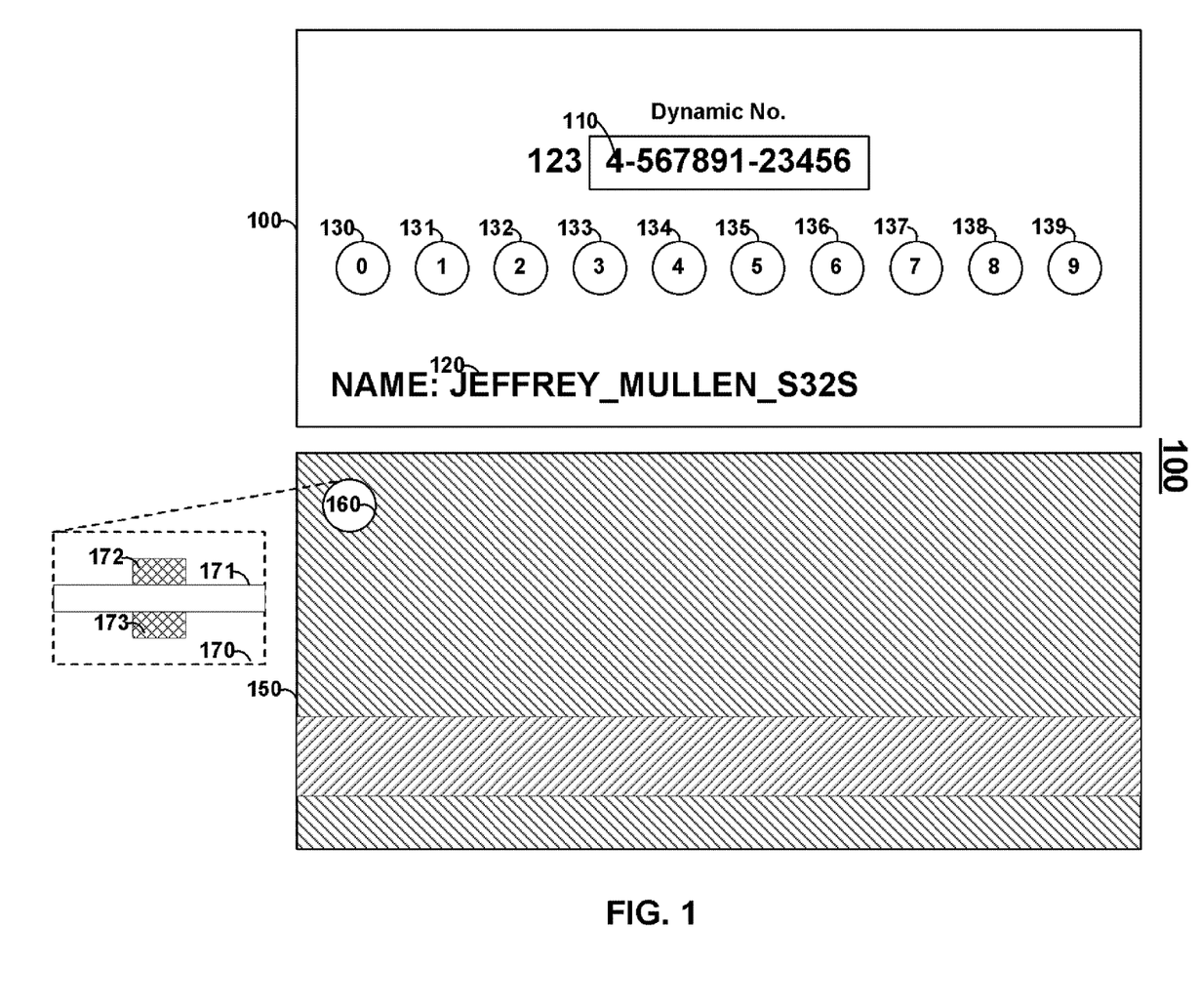
FIG. 1 is an illustration of cards constructed in accordance with the principles of the present invention.

FIG. 1 shows card 100 that may include a display that may display dynamic number 110, which may be utilized, for example, as a credit card number or as part of a credit card number (e.g., with a static portion of a credit card number that proceeds dynamic number 110). Persons skilled in the art will appreciate that a dynamic number may take any forms such as, for example, a dynamic credit card number, a dynamic verification code number, and/or a dynamic security code number. For example, card 100 may include a dynamic credit card number and a dynamic verification code (e.g., a 15 digit credit card number and a 4 digit verification code or a 16 digit credit card number and a 3 digit code).

Identification information 120 may be provided on card 100. Accordingly, for example, a dynamic number may be provided for a particular period of time according to a coding scheme for that particular period of time. Thus, the identification information, time, and dynamic information may be transmitted via manual entry of that information (e.g., through a payment information input process on an online store) or via a magnetic emulator (e.g., through an in-store magnetic stripe reader). A remote server may receive such information and verify whether the dynamic information is correct for particular identification information and a particular period of time. A remote server may look at particular parts of a payment number (e.g., a static portion of a payment card number) and may determine whether another part of that payment number (e.g., a dynamic number) is valid for that particular part for a particular period of time. A number, or portion of a number, may be changed based on use (e.g., as a result of a user pressing a button or a read-head detector determining the presence of a magnetic stripe read-head).

Input buttons 130-139 may be provided such that manual input may be received and processed by card 100. Manual input buttons 130-139 may be utilized in a variety of ways. For example, an individual may be issued with a private personal identification number (PIN) to turn the card ON and/or to activate a feature. Thus, buttons 130-139 may be utilized to confirm that the individual issued the card is utilizing the card and its various features. In doing so with a credit card, for example, the amount of fraud associated with physical card theft may be minimized. Accordingly, a dynamic credit card number may be generated (e.g., coded) upon successful entry of an appropriate PIN. Additionally, for example, manual input keys 130-139 may be used to navigate through a list of options or initiate features. For example, button 130 may turn card 100 ON/OFF. Button 131 may turn display 110 ON/OFF. Button 132 may turn an emulator located on card 100 ON/OFF. Persons skilled in the art will appreciate that a credit card number may be coded based on time and transmitted with an identification number to a verification server. In turn, the verification server may decode the number based on time and identification number to verify, for example, a credit card transaction.

Card 150 may include button 160 which may, for example, be in the form of an aperture. For example the aperture may be defined in material 171 and may include sensors 172 to 173 to determine if a user presses around the aperture. Accordingly, a person pinching the aperture with two fingers may cause an electrical connection between sensors 172 and 173 via the skin of two fingers touching via the aperture. Accordingly, for example, pinching may result in the recognition of the activation of a button while just touching one side may not cause the activation of a button. In doing so, the number of times a button may become active by accident (e.g., while in a user's wallet) may be decreased.

Figure 2:
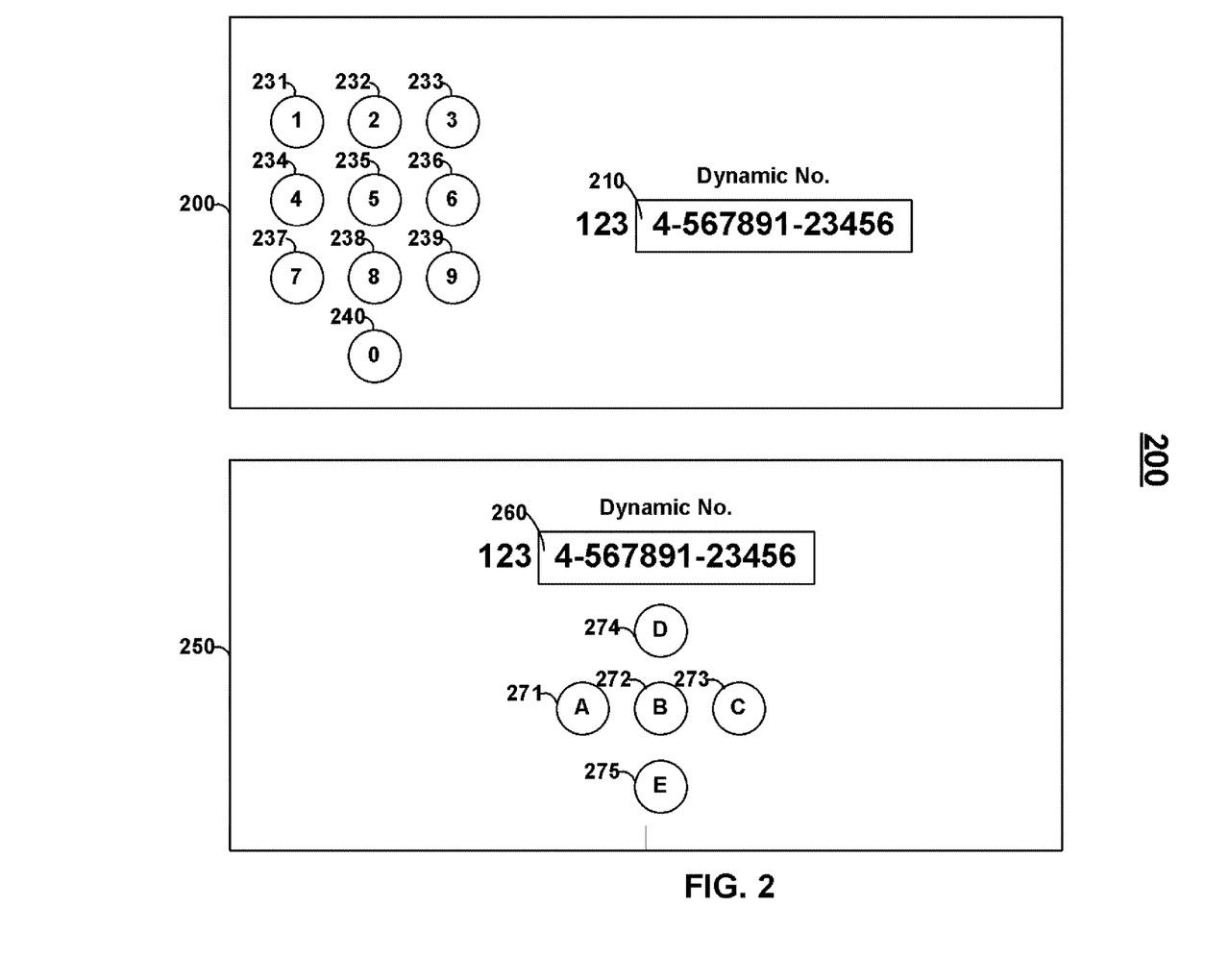
FIG. 2 is an illustration of cards constructed in accordance with the principles of the present invention.

Card 200 includes buttons 231-240. Buttons 231-140 may be aligned vertically or horizontally (e.g., with respect to the bottom of a card) or, for example, substantially in a block or circle.

Card 250 may include buttons 271-275, which may be aligned, for example, in the shape of a directional up-down/left-right pad with a centralized button. Accordingly, buttons 271-275 may be used to navigate through a list of options. Accordingly, for example, display 260 may include multiple lines of alphanumeric text and buttons 271-275 may be used to 20 navigate through the text. Additionally, a personal identification code may be provided and may be entered via buttons 217-275 (e.g., 'A-B-B-D-E-A' may be entered to turn the card ON or turn a feature ON.

Figure 3:
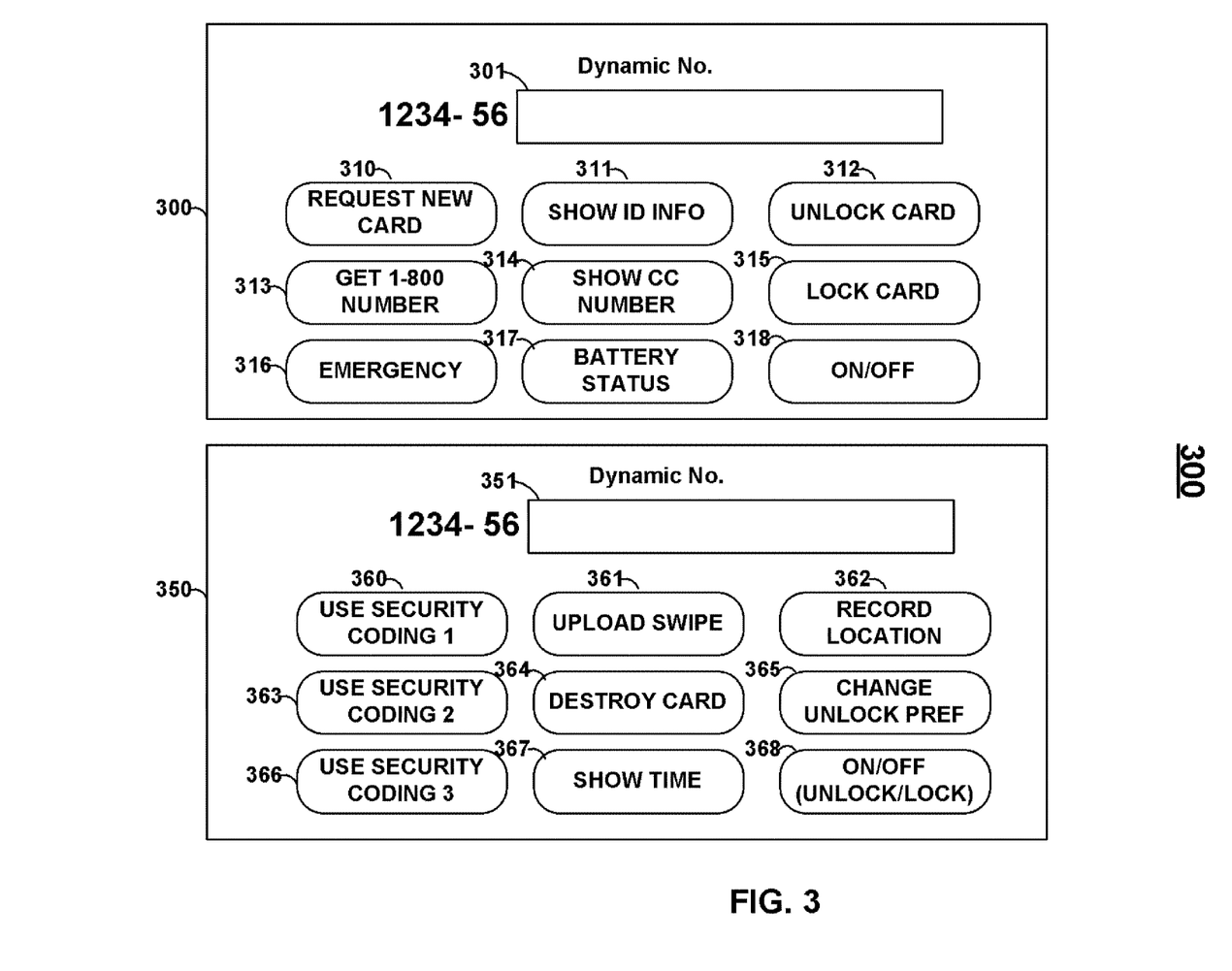
FIG. 3 is an illustration of cards constructed in accordance with the principles of the present invention.

Card 300 may be included with buttons 310-319. Buttons 310-319 may also be associated with digits 0-8, respectively. Another button may be added and associated with, for example, digit 9 such that a digit-based keypad is provided. A digit may be pressed multiple times in succession such that alphanumeric data may be entered. Button 310 may be utilized to request a new card. In pressing button 310, or any button, information representative of this request may be displayed so that the information may be entered online or transmitted through a reader via a magnetic emulator. The receipt of such information may cause the desired action to occur (e.g., a new card may be sent).

Button 311 may be pressed to display and/or emulate identification information associated with the user of the card (or allow a user to LOGIN/LOGOUT of the card so that multiple users can utilize the card). Button 312 may be used to unlock the card. For example, button 312 may be pressed, then a personal identification code may be entered, then button 312 may be pressed again. If the correct personal identification code was entered, for example, then a feature (e.g., card unlocking) may occur. A process may, for example, include determining if button 312 is pressed and the entrance of a correct personal identification code without, for example, determining a subsequent entry of button 312. Such a process may, for example, allow a user to expedite entry of a personal identification code. If a user enters an incorrect personal identification code, for example, nothing may happen or the user may be prompted, via the display, to re-enter the code. After a particular amount of time waiting for the next manual input for a code, the processor may return to looking for the first manual input representative of a correct code (e.g., after 5 seconds). After an incorrect code is received, a processor may return to looking for the entry of the first manual input representative of a correct code (e.g., the first button of an appropriate code). Moreover, for example, a particular number of codes entered in error may permanently lock the card or may lock the card until a period of time has passed (e.g., 5 minutes). Button 313 may be added to present the 1800 number for the card on the display. Button 314 may be utilized to show, as well as magnetically emulate the a dynamic number (e.g., the dynamic credit card number for a period of time and for a particular person). Button 315 may be utilized for to lock a card. Button 316 may be utilized to transmit, for example, an emergency alert such as an alert that the card is about to be stolen or someone is in trouble (and may, for example, be transmitted upon swiping of a card). Button 317 may be utilized to display/magnetically emulate battery status. Button 318 may be utilized to turn the card ON/OFF. Persons skilled in the art will appreciate that, for example, additional information (e.g., alerts, battery information, card replacement requests) may be communicated as discretionary data in communicated payment information or may be communicated in a separate information transmission. Similarly, such information may be embedded in non-discretionary data information in communicated payment information.

Card 350 may be utilized. Buttons 360-368 may be provided. Buttons 360, 363, and 366 may each be associated with a different coding scheme. Pressing button 360, 363, and 366 may cause a number (e.g., credit card or security number) to be generated differently. Thus, for example, a company may issue security cards and may associate different button switch different levels of security or may rotate between the coding schemes or may allow for a new coding scheme to be used if a coding scheme is compromised. Button 361 may be utilized to upload information at upload locations (e.g., upload new software). Accordingly, circuitry may be included to receive information from a swipe.

Button 364 may be utilized to destroy a card (e.g., burn out components). Persons skilled in the art will appreciate that the functions of various buttons may be triggered autonomously upon particular determinations of a processor. For example, a processor may determine that someone is trying to break through the casing of a component (e.g., a memory) and may autonomously burn out components or perform other tasks (e.g., erase memory) as a result of the determinations. A processor may write information to a memory when the processor detects an fraudulent attack on a card by, for example, erasing a portion of data (e.g., payment card number(s)), erasing all of the data, or changing the data (e.g., replace a payment card number with a number indicative of a fraudulent activity) on a memory.

Button 367 may be utilized to show time (e.g., the current time) on a display. A clock may be provided on card 350 such that time may be kept. Such a clock may be provided with its own battery such that the clock may continue to keep track of time even when, for example, a processor is OFF. Persons skilled in the art will appreciate that a card may be ON when the card is delivered to a user but that a processor may be in a hibernation mode. Accordingly, for example, an ON/OFF button (or an unlock code) may wake that processor out of such a hibernation mode.

Button 363 may be utilized to record (e.g., store in memory), display on a display, and communicate through a dynamic magnetic communications device (e.g., a magnetic emulator or encoder) a location of the card or a history of locations of a card. Accordingly, for example, a locating device (e.g., GPS receiver) may be provided on a card. A transmitter may be provided that may communicate a signal that multiple remote receivers may receive (e.g., mobile phone base stations) such that the location of a card may be determined (e.g., via a triangulation process).

Button 365 may be utilized to change the unlocking preferences (e.g., change a personal identification code). For example, a user may be prompted to enter the user's current personal identification code, then be prompted to enter the user's new personal identification code, and then be prompted to confirm entry of the user's new personal identification code. If the two new personal identification codes match, then, for example, the personal identification code for a user may be changed. A card may be provided with a default personal identification code. Button 368 may be utilized on turn a card ON/OFF.

Figure 4:
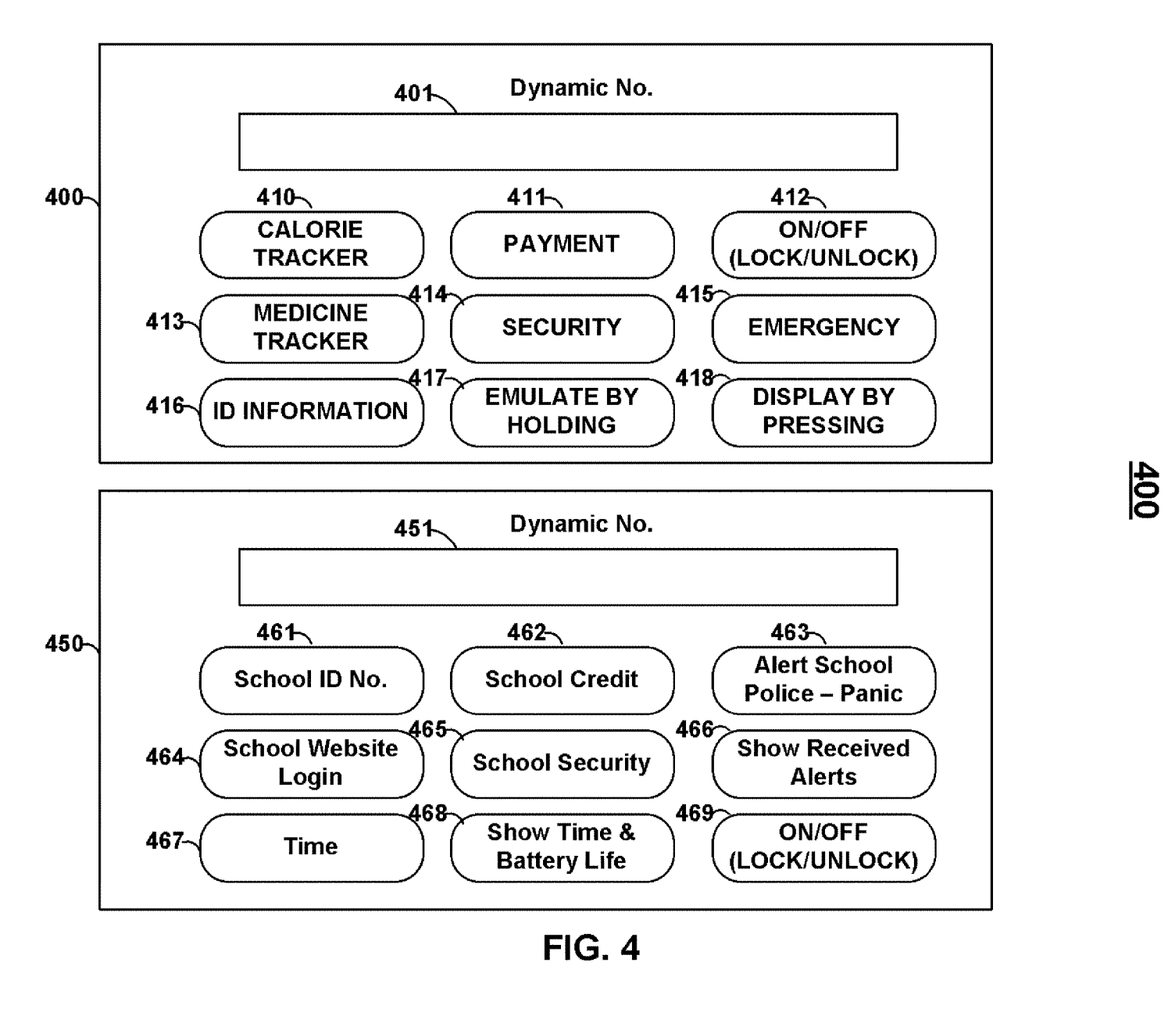
FIG. 4 is an illustration of cards constructed in accordance with the principles of the present invention.

FIG. 4 shows card 400 which may include buttons 410-418. Button 410 may include a calorie tracker such that a user can enter in calories he/she eats per day. Thus, whenever a card is swiped via a magnetic stripe reader, or otherwise communicates data to a card reader or device, the calorie information may be entered into a database which can be utilized to populate a webpage (e.g., a calorie tracker webpage).

Button 413 may be utilized as a medicine tracker (e.g., to track the type and number of pills taken). Information may be displayed on display 401 that a user may enter such that the information may be associated with information entered by a user. For example, display 401 may provide an alphanumeric word "A342F2432S" that may be associated with, for example, 100 calories for breakfast and 300 calories for lunch on Dec. 12, 2007. This word may be entered on a website such that the information associated with the word may be used to populate the website (e.g., the calorie tracker).

Button 416 may be used to display identification information (e.g., name and phone number of card user). Accordingly, for example, someone that finds card 400 may press button 416 to determine the owner of card 416 as well as other information (e.g., phone number and email address).

Button 411 may be used for payment. Accordingly, for example, a payment number may be displayed on a display (along with additional payment data such as a payment security code). A dynamic magnetic communications device (or other device operable to communicate to a card reader) may also transmit information that includes such a payment number and additional payment data.

Button 414 may be used for security (e.g., an online login). Accordingly, for example, a user may press button 414 and may be provided with a code (e.g., an access security code) such that the user may enter particular portions of a website (e.g., a webpage associated with a user's banking account). Such an access code may be displayed to a user such that a user may enter the code into a keypad at a lock such that the lock is opened upon received of the correct code. Similarly, such an access security code may be, for example, communicated via a dynamic magnetic communications device (e.g., a magnetic emulator or magnetic encoder) as well as other reader communications devices (e.g., RFIDs and IC chips such as EMV chips). Such codes may change based on time or based on use (e.g., every time button 414 is pressed by a user).

Button 417 may be used to magnetically emulate information by holding button 416 such that data may be communicated via a magnetic emulator to a magnetic stripe reader. For example, button 410 may be pressed and then button 417 may be pressed to emulate information associated with a calorie tracker. Button 412 may be used, for example, to turn card 400 ON/OFF and/or UNLOCK/LOCK card 400. Button 415 may be utilized as an emergency alert (e.g., a panic button). Accordingly, for example, a student may press emergency button 415 and swipe his/her card into a magnetic stripe reader and the appropriate authorities (e.g., police) may be alerted of the magnetic stripe reader, and its location, from which an emergency was initiated (and the identity of the person that initiated an emergency. In this manner, a police button, firefighter button, and ambulance button may be utilized.

Alternatively, for example, a doctor button, a nurse button, or a food button may be utilized for hospital cards. Button 418 may be utilized to display information on display 401 while the button is pressed. Accordingly, for example, calorie tracker 410 may be utilized and then button 418 may be pressed to display information associated with calorie tracker 410.

FIG. 4 shows card 450 that may include, for example, buttons 461-469. Button 461 may be used to display, as well as magnetically communicate via a magnetic emulator to a magnetic stripe reader, school identification information. Button 462 may be utilized to display, as well as communicate through a dynamic magnetic communications device, school credit information. Button 464 may be utilized to display, as well as communicate through a dynamic magnetic communications device, website login information. Button 467 may be utilized to display emulate, for example, time information. Button 466 may be utilized to show alerts that are received. For example, a receiver may be included in a card that may receive wireless alerts. Accordingly, for example, students may be alerted of a school-related risk/danger/information (e.g., bomb threat, fire, or school cancelled due to snow) and may be shown this information via display 451. Button 451 may be utilized to show, for example, the most recent alert and/or scroll through alerts. Button 469 may be utilized, for example, to turn card 450 ON/OFF and/or UNLOCK/LOCK card 450.

Figure 5:
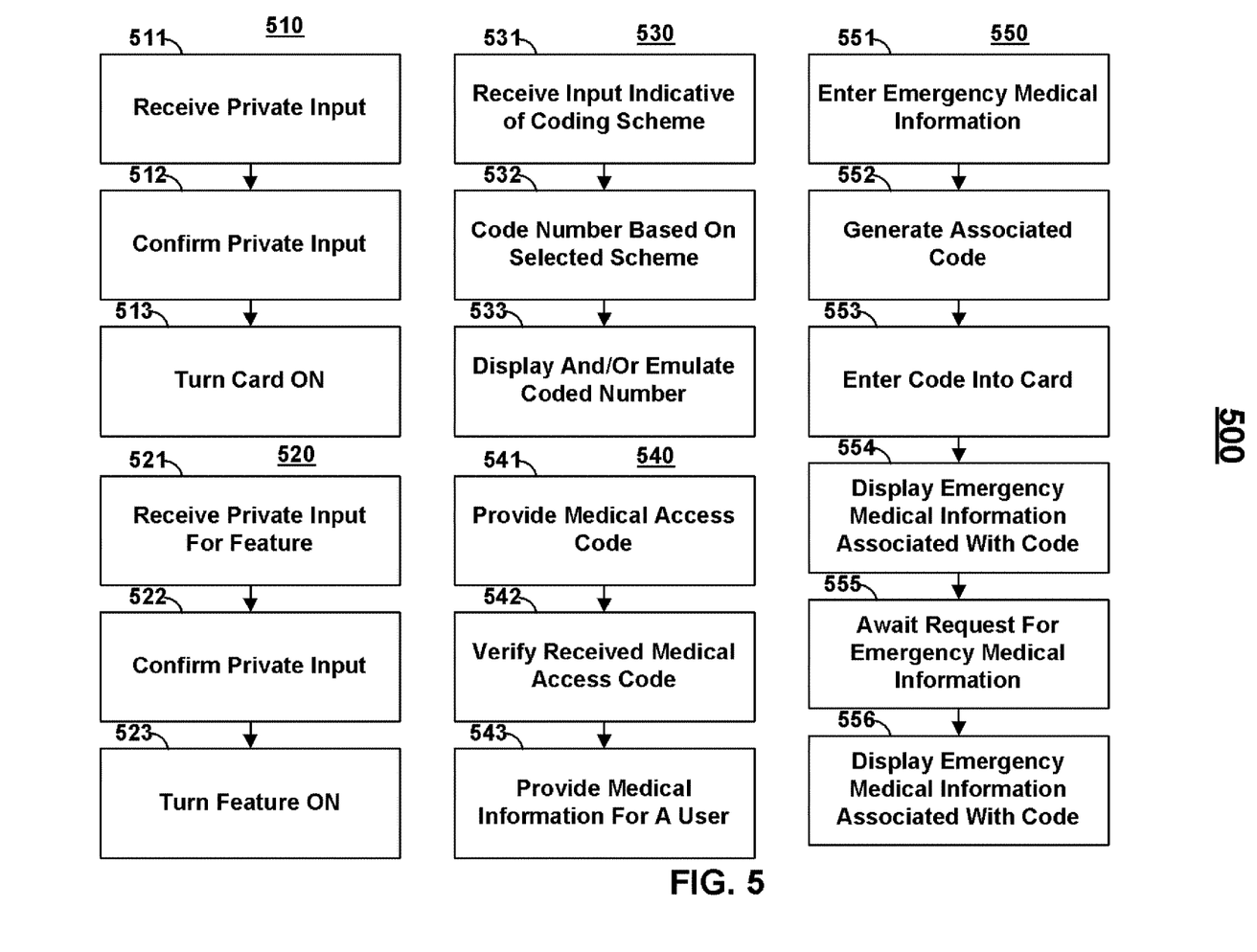
FIG. 5 is an illustration of process topologies constructed in accordance with the principles of the present invention.

FIG. 5 shows flow charts 510, 520, and 530. Flow chart 510 may include, for example, step 511, in which private input (e.g., private identification information) is received. This information may be confirmed, for example, in step 512. Additionally, confirmation of the correct private number may turn a card ON (e.g., allow information to be displayed/emulated) in step 513.

Flow chart 520 may be included. Step 521 may be provided, in which, for example, private input is received for a particular feature. This input may be confirmed in step 522. Accordingly, for example, a feature may be turned ON in step 523. Flow chart 530 may be included. Step 531 may be provided, in which input indicative of a particular coding scheme is received. A number (e.g., website login and/or credit card) may be coded or generated (e.g., from a hash table associated with a particular input) in step 523. The coded, generated, and/or retrieved information may be displayed and/or communicated through a magnetic emulator in step 533.

Flow chart 540 may be provided and may be utilized, for example, in conjunction with a medical card and medical information retrieval system. For example, medical information may be stored on the memory of a card. Such medical information may be, for example, a user's height, weight, eye color, blood type, previous medical conditions, previous medications taken, current medical conditions, current medications taken, allergies, doctor contact information, as well as contact information for an emergency contact person.

Persons skilled in the art will appreciate that a user may control access to the user's medical information by, for example, keeping the medical information in his/her pocket and under his/her control at all times. (e.g., similar to the protection afforded to car keys and house keys). In the case of an emergency (e.g., a car accident), first responders may look for the user's medical card in order to gain access to the user's medical information. Such a medical card may take the form of, for example, an identification card (e.g., a driver's license or passport). A sticker may be placed on a card or device (e.g., a mobile telephone or identification card) stating that a user has a medical card in his/her wallet (e.g., as well as the location of the card such as on the left-hand side of the wallet). A medical card may, for example, be taken by a first responder and may display a passcode for the responder to enter onto a website in order for the responder to obtain the user's medical information. Identification information may be permanently displayed on the card (e.g., printed or embossed) and this identification may be entered into a website along with a user. Instructions for accessing the medical information may be printed or embossed on a card or other device. Such an access security code may, for example, change based on time or use (e.g., press of a particular button or particular buttons). A first responder may be prompted by a website, for example, to enter in a responder's username and password such that the responder can be identified as a responder that may access the medical information of a user. Medical information stored on a remote server may include, for example, pictures (e.g., of a birth certificate and bodily parts at various times), x-rays, medical reports, as well as any other type of medical information. A medical card may also store such images and other data.

Flow chart 540 may include, for example, a card (or other device) providing a medical access code in step 541. Step 542 may be included, in which a medical access code is verified (e.g., on a remote server). Step 543 may be provided, in which medical information for a user may be provided as the result of the verification of a correct access code. An access code may be, for example, a five, six, seven, or eight digit code (e.g., "834699"). Persons skilled in the art will appreciate that a card may include, for example, medical information. Such medical information may be displayed, for example, by a user pressing a particular button. The information may be scrolled left/right as well as up/down using the same button or additional buttons. For example, a first line of data may be "Blood Type: B" and a second line of data that can be scrolled down to using a button may be "Allergies: None"

Flow chart 550 may be provided. Step 551 may be provided, in which a user may go to a website or a graphical user interface on a device and enter in his/her emergency medical information. Such information may be, for example, pre-populated with the websites prior knowledge as to the user's emergency medical information. Such information may be changed by a user. The entry of medical information may take many forms. For example, the entry of medical information may be done through the selection of options. For example, a user may be provided with a list of allergies and may select those allergies that apply to a user. A user may then, for example, generate a code in step 552. Such a code may be, for example, associated with the particular combination of selections that user made. A user may then, for example, enter this code into his/her medical card using buttons on that medical card. In this manner, the medical card may include data on a memory that may recognize the code and may display, at a user's request, the medical information associated with that code (e.g., step 554). Accordingly, for example, a user may customize and update his/her payment card without having to connect the user's payment card to a computer (e.g., via a USB port). A card may wait for a request for emergency medical information (e.g., step 555) and may provide the emergency medical information as a result of receiving the request (e.g., step 556).

Figure 6:
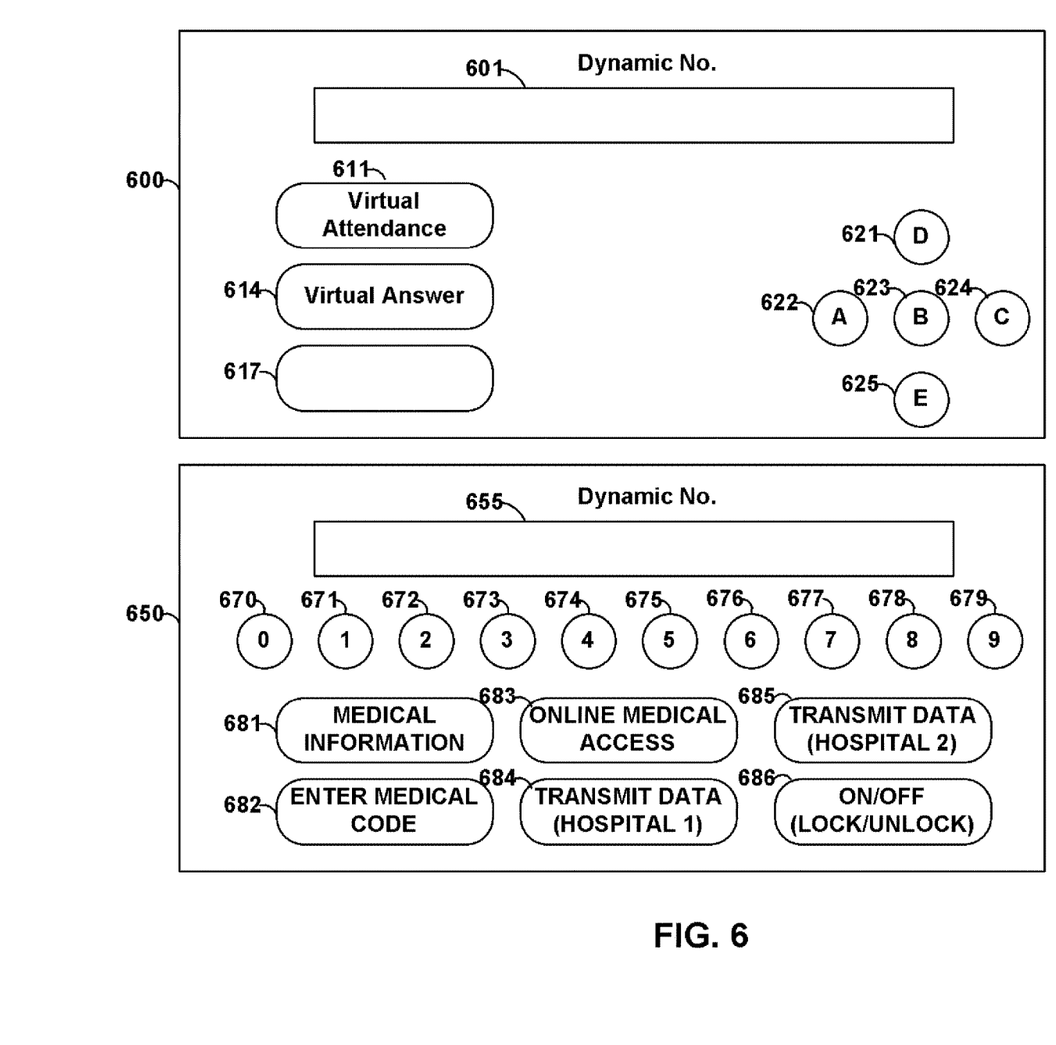
FIG. 6 is an illustration of cards constructed in accordance with the principles of the present invention.

FIG. 6 shows card 600 which may include buttons 611, 614, and 617. Button 611 may be utilized for virtual attendance. A user may press button 611 and transmit identification information (e.g., either wirelessly or via a magnetic emulator) to a server such that attendance may be recorded. Similarly, button 614 may be utilized to provide a virtual answer to a question. For example, button 614 may be pressed, a button associated with answer "B" may be pressed, button 614 may be pressed again, and then a card may be swiped and information associated with the answer transmitted (e.g., via a magnetic emulator) to a server for further processing. Buttons 621-625 may be utilized, for example, to enter responses into a card so that the responses may be displayed visually or communicated via a magnetic emulator.

Card 650 may be provided with buttons 670-679 and 681-686. Button 681 may be utilized, for example, to display medical information on a display of card 650. Button 682 may be utilized, for example, to prompt a processor on card 650 that a code associated with medical information is about to be entered. Button 683 may be utilized, for example, to provide (e.g., via a display) a code for accessing a user's online medical record. Button 684 may be utilized, for example, to communicate information (e.g., insurance information) in one format to a particular hospital that accepts that format. Button 685 may be utilized, for example, to communicate the same information (e.g., the same insurance information) in a different format to a different hospital that accepts that different format. Button 686 may be utilized to turn a card ON/OFF.

Figure 7:
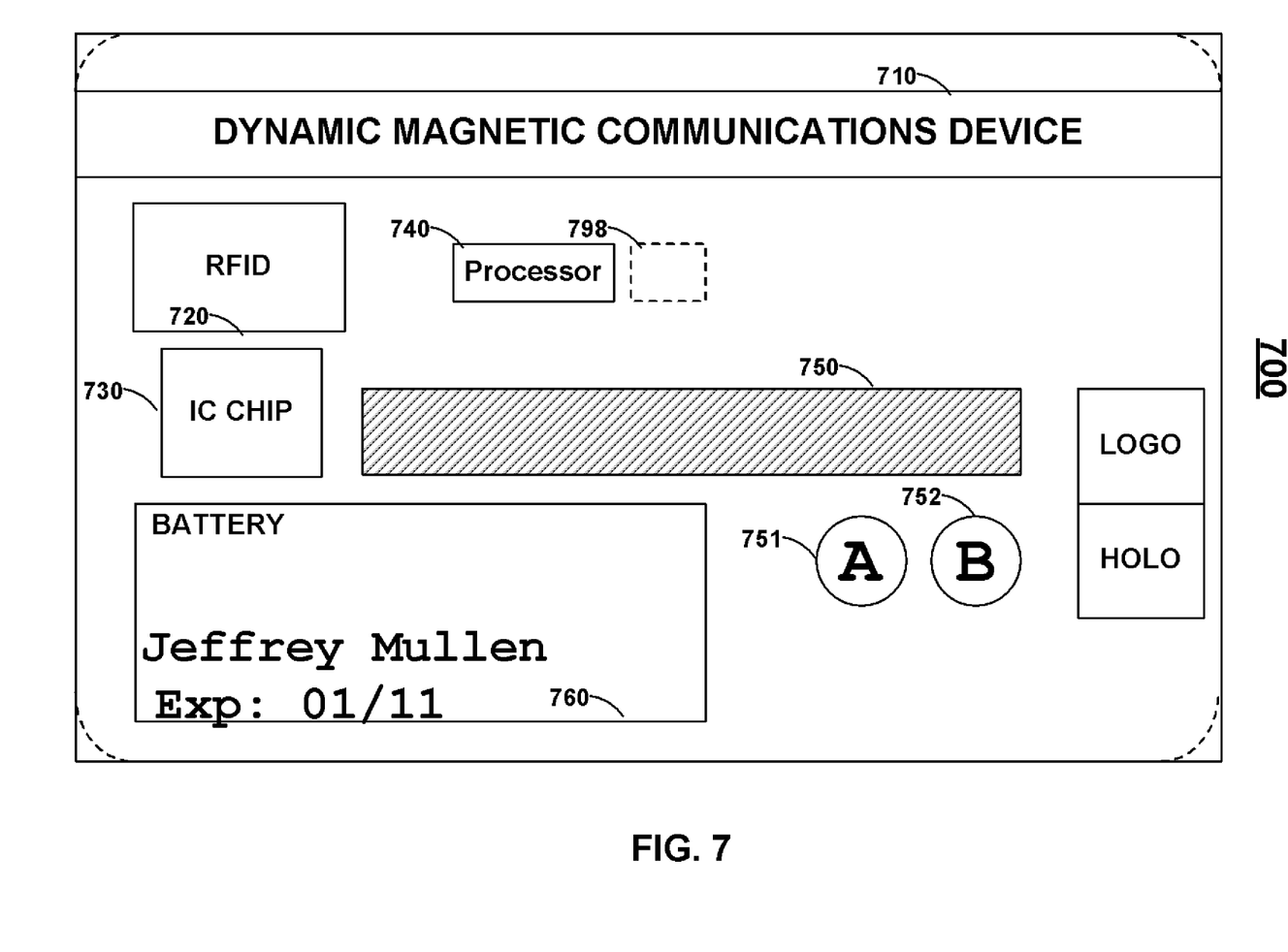
FIG. 7 is an illustration of a card constructed in accordance with the principles of the present invention.

FIG. 7 shows card 700 that may include, for example, one or more IC chips 730 (e.g., EMV chips), RFID antennas 720, processors 740, displays 750, dynamic magnetic communications devices 810 (e.g., magnetic encoders and/or magnetic emulators), batteries 760, and buttons 751 and 752. Additional circuitry 798 may be provided which may be, for example, one or more oscillators or emulator driving circuits. Persons skilled in the art will appreciate that button 751 may, for example, be utilized by a user to select one encryption algorithm for a number displayed on display 750 while button 752 may be utilized by a user to select a different encryption algorithm. Persons skilled in the art will appreciate that the components of card 700 may be provided on either surface of a card (e.g., a front or rear surface of the card) or inside of a card. A logo (e.g., of a card issuer) and logo may be provided on either surface of a card.

A button, such as button 751, may be utilized, for example, to display a number. Such a number may be, for example, encrypted from a secure number based on time or use. For example, one-time use numbers (e.g., a payment number or code) may be retrieved from a list of numbers on memory each time button 751 is pressed and displayed on display 750. A processor may only go through each number once on a list. A registration process may be provided in which a user may be requested to enter in a sequence of numbers such that a remote server may validate the card and learn where in a sequence of a list a card currently resides. Numbers may be repeated on a list or may only occur once on a list. All of the numbers available by the length of the number may be utilized by the list or only a portion of the numbers available by the length of the number may be provided by the list. A secret number may be encrypted on a card and a verification server may also have knowledge of this secret number. Accordingly, the remote server may perform the same encryption function as the card on the secret number and verify that the resultant encrypted number is the same as the resultant encrypted number on a card. Alternatively, for example, the remote server may decrypt the received encrypted number to determine the authenticity of the encrypted number and validate an activity (e.g., validate a security access request or a purchase transaction).

Persons skilled in the art will appreciate, for example, that a card may include an IC chip (e.g., EMV chip), RFID, and a dynamic magnetic communications device (e.g., a magnetic emulator or encoder). The same information may be communicated through, for example, any number of such devices (e.g., a dynamic magnetic communications device, RFID, and an EMV chip). A central processor may cause each device to communicate the information (in the same format or a different format). Each component may have its own processor or driving circuitry. Such individual processors or driving circuitry may be coupled to a central processor. An EMV chip may be utilized, for example, to provide control signals to other devices (e.g., circuitry driving a display as well as a dynamic magnetic communications device). Such an EMV chip may receive signals provided by one or more buttons to determine, for example, that a particular button, or sequence of buttons, was pressed by a user.

Persons skilled in the art will appreciate that a read-head housing may include, for example, multiple read-heads. A read-head detector may, more generally, detect a read-head housing and, in doing so, detect a read-head.

Figure 8:
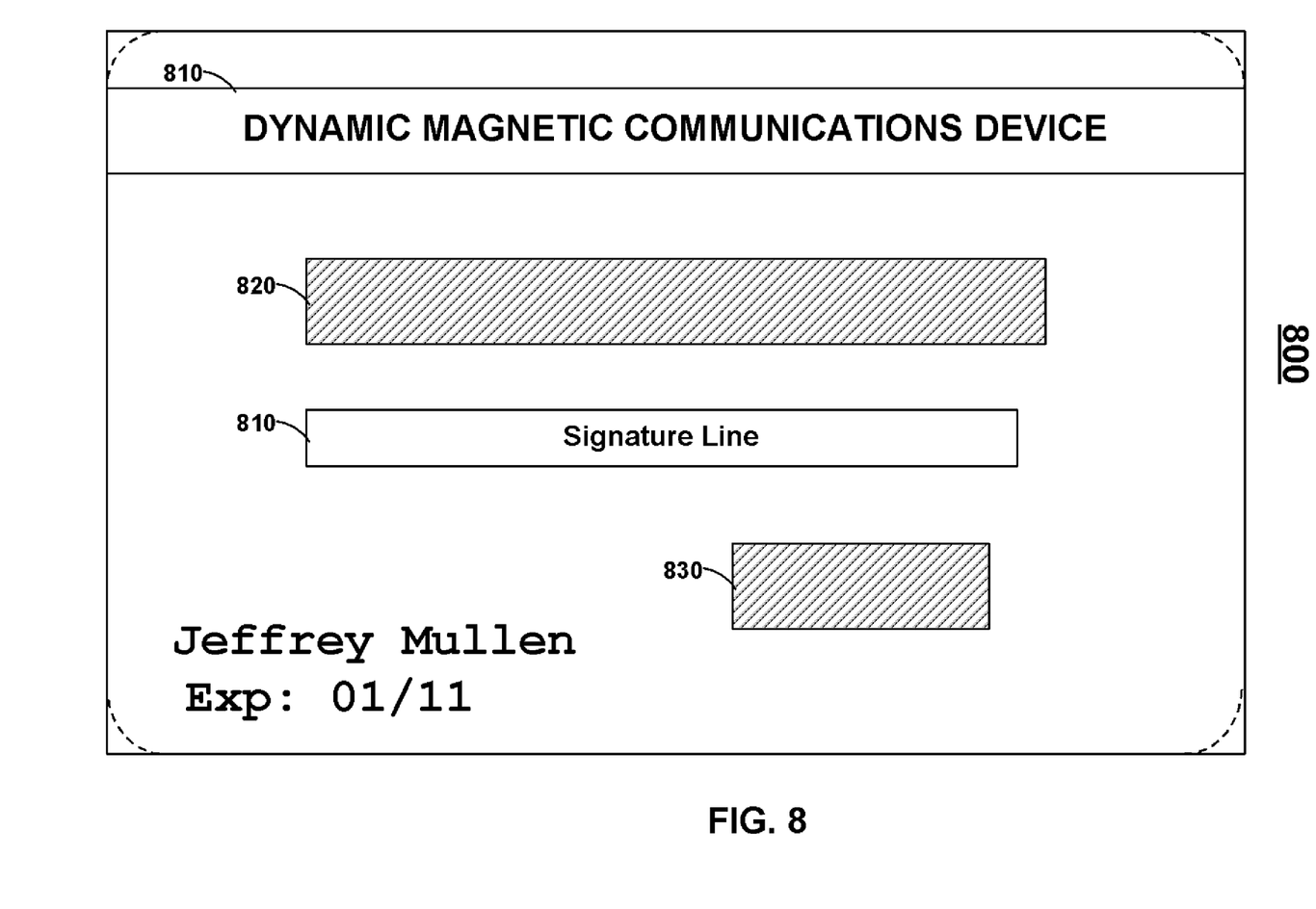
FIG. 8 is an illustration of a card constructed in accordance with the principles of the present invention.

FIG. 8 shows card 800 that may include, for example, signature area 810 that may include a material operable to receive marks from a pen (e.g., a signature). Card 800 may also include, for example, displays 820 and 830. Display 820 may, for example, display a payment number while display 830 displays a security code (e.g., for online purchase authentication). Display 820 as well as display 830 may be utilized on the same side as, for example, dynamic magnetic communications device 810.

Figure 9:
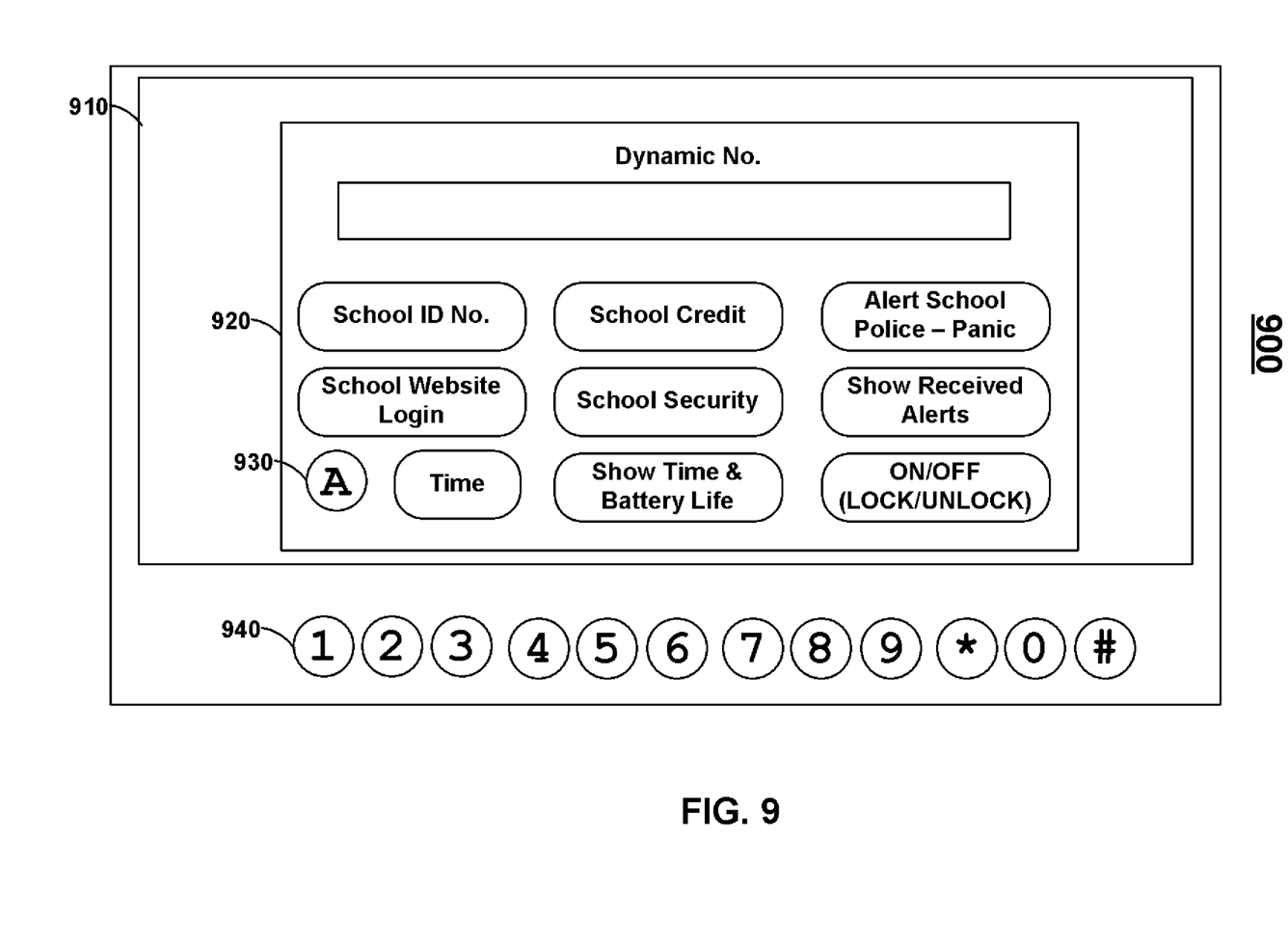
FIG. 9 is an illustration of a personal electronic device constructed in accordance with the principles of the present invention.

FIG. 9 shows personal electronic device 900 which may be, for example, a portable telephonic device, portable media player, or any type of electronic device. Persons skilled in the art will appreciate that the functionality of a card may be provided on a personal device and displayed through a graphical user interface. Personal electronic device 900 may include, for example, user inputs 940 and display 910. Virtual card 920 may be displayed on display 920. Display 920 may be a touch-sensitive display such that, for example, virtual button 930 may be provided on virtual card 920. Persons skilled in the art will appreciate that cards may be provided as virtual cards and a user may interact with such virtual cards in order to provide a variety of functions. Personal electronic device 900 may communicate to a card reader such as, for example, an RFID reader.

A display may be bi-stable or non bi-stable. A bi-stable display may consume electrical energy to change the information displayed on the bi-stable display but may not consume electrical energy to maintain the display of that information. A non bi-stable display may consume electrical energy to both change and maintain information on the non bi-stable display. A display driving circuit may be provided, for example, for a bi-stable display (or a non bi-stable display). Such a display driving circuit may step-up a supply voltage (e.g., 1-5 volts) to a larger voltage (e.g., 6-15 volts) such that a bi-stable display may change displayed information. A controller (e.g., a processor) may be utilized to control such a display driving circuit. Persons skilled in the art will appreciate that a display may be configured to display numerical data or alphanumerical data. A display may also be configured to display other indicia (e.g., the image of a battery and its remaining life).

Persons skilled in the art will appreciate that a dynamic magnetic communications device (e.g., a magnetic emulator or magnetic encoder) may be fabricated, either completely or partially, in silicon and provided as a silicon-based chip. Other circuitry (e.g., driving circuitry) may also be fabricated on such a silicon-based chip. A processor, such as a processor for controlling a magnetic communications device, may be, for example, a programmable processor having on-board programmable non-volatile memory (e.g., FLASH memory), volatile memory (e.g., RAM), as well as a cache. Firmware as well as payment information (e.g., dynamic numbers) may be, for example, communicated from a programming device to a processor's on-board programmable non-volatile memory (e.g., a FLASH memory) such that a card may provide a variety of functionalities. Such a processor may also have one or more power-saving operating modes, in which each operating mode turns OFF a different set of circuitry to provide different levels of power consumption. One or more power-savings modes may turn OFF, for example, one or more clocking circuitry provided on a processor. An Application-Specific Integrated Circuit (ASIC) may also be included in a card or other device to provide, for example, processing, dynamic magnetic communications, as well as driving capabilities.

Persons skilled in the art will also appreciate that the present invention is not limited to only the embodiments described. Instead, the present invention more generally involves dynamic information. Persons skilled in the art will also appreciate that the apparatus of the present invention may be implemented in other ways then those described herein. All such modifications are within the scope of the present invention, which is limited only by the claims that follow.

What is claimed is:
1. A card comprising:
   a plurality of buttons;
   a dynamic magnetic communications device operable to communicate at least one track of magnetic stripe information to a read head of a magnetic stripe reader, the dynamics communication device being fabricated on a first printed circuit board; and an EMV chip, mounted to a second printed circuit board, for determining whether a match occurs between a sequence of manual input entered into said plurality of buttons and a stored sequence, wherein data is displayed on a display if said match occurs.

2. The card of claim 1, wherein said display is non bi-stable.

3. The card of claim 1, wherein said display is bi-stable.

4. The card of claim 1, wherein said display is located above said plurality of buttons.

5. The card of claim 1, wherein said display is located to the right of said plurality of buttons.

6. The card of claim 1, further comprising an RFID.

7. The card of claim 1, further comprising an RFID and a battery.

8. The card of claim 1, further comprising a card reader communications device.

9. The card of claim 1, further comprising a magnetic stripe read-head detector.

10. The card of claim 1, further comprising a dynamic magnetic stripe communications device.

11. The card of claim 1, further comprising a card reader communications device for communicating a data block.

12. The card of claim 1, further comprising a card reader communications device for communicating a data block after said match occurs.

13. The card of claim 1, further comprising a card reader communications device for communicating a data block serially.

14. The card of claim 1, wherein said sequence of manual input is a personal identification number.

15. The card of claim 1, wherein said data includes at least a portion of a payment number.

16. The card of claim 1, wherein said data includes at least a portion of a credit card number.

17. The card of claim 1, wherein said data includes at least a portion of a debit card number.

\* \* \* \* \*